(12) United States Patent
McGinity et al.

(10) Patent No.: US 6,488,963 B1
(45) Date of Patent: Dec. 3, 2002

(54) HOT-MELT EXTRUDABLE PHARMACEUTICAL FORMULATION

(75) Inventors: James W. McGinity; Feng Zhang, both of Austin, TX (US)

(73) Assignee: The University of Texas System, Austin, TX (US)

(*) Notice: Subject to any disclaimer, the term of this patent is extended or adjusted under 35 U.S.C. 154(b) by 0 days.

(21) Appl. No.: 09/260,694

(22) Filed: Mar. 2, 1999

Related U.S. Application Data

(60) Provisional application No. 60/020,623, filed on Jun. 26, 1996.

(51) Int. Cl.[7] .............................. A61K 9/10; A61K 47/34
(52) U.S. Cl. ........................................ 424/486; 514/953
(58) Field of Search ................. 424/484, 486, 424/468, 457, 500, 422; 514/953, 964, 772.7

(56) References Cited

U.S. PATENT DOCUMENTS

| | | | |
|---|---|---|---|
| 3,806,603 A | 4/1974 | Gaunt et al. | 424/364 |
| 4,629,621 A | 12/1986 | Snipes | |
| 4,744,976 A | 5/1988 | Snipes | |
| 4,764,378 A | 8/1988 | Keith et al. | 424/435 |
| 4,774,074 A | 9/1988 | Snipes | |
| 4,806,337 A | 2/1989 | Snipes | |
| RE330,943 | * 10/1989 | Schiraldi | |
| 5,004,601 A | 4/1991 | Snipes | |

FOREIGN PATENT DOCUMENTS

| | | |
|---|---|---|
| EP | EP0177893 | 4/1986 |
| EP | 0598606 A1 | 5/1994 |
| WO | WO93/10758 | 6/1993 |
| WO | WO93/11749 | 6/1993 |
| WO | WO94/08567 | 4/1994 |
| WO | WO95/22319 | 8/1995 |

OTHER PUBLICATIONS

El-Egakey et al., *Pharm. Acta. Helv.* (1971), 46, 31–52.
Rippie et al., *J. Pharm. Sci.* (1969), 428–431.
Mank et al., *Pharmazie* (1989), 44, 773–776.
Mank et al., *Pharmazie* (1990), 45 592–593.
Follonier, et al., *Drug Develop. and Indust. Pharm.*, (1994), 20(8), 1323–1339.
Remington's Pharmaceutical Sciences, 17th ed. (Mack Publishing Co., Easton, PA, 18042, 1985).
Thoma, Von K. et al., *Pharm. Ind.* 51, Nr. 6 (1989).
Janicki, Stanislaw et al., *Acta Pharm. Tecnol.* 33(3) 154–155 (1987).
Mesiha, Mounir et al., *Drug Development and Industrial Pharmacy*, 19(8), 943–959 (1993).

* cited by examiner

*Primary Examiner*—Edward J. Webman
(74) *Attorney, Agent, or Firm*—Gardere Wynne Sewell LLP; Sanford E. Warren, Jr.; Edwin S. Flores

(57) ABSTRACT

The present invention relates to pharmaceutical formulations comprising a hot-melt extrudable mixture of a therapeutic compound and a high molecular weight poly(ethylene oxide) in an essentially non-film like preparation. In some embodiments, the formulation further comprises poly (ethylene glycol). The present invention also includes efficient methods for hot-melt extruding pharmaceutical formulations in essentially non-film preparations.

6 Claims, 1 Drawing Sheet

HOT-MELT EXTRUDABLE PHARMACEUTICAL FORMULATION

The present application claims the benefit of PCT/US 97/11206, filed Jun. 24, 1997 which claims the benefit of of U.S. Pat. No. 60/202,623, filed Jun. 26, 1996.

FIELD OF THE INVENTION

The present invention relates to the field of poly(ethylene oxide) (PEO) based hot-melt extrudable pharmaceutical formulations that are not film-like preparations. The invention relates more specifically to non-film formulations which have been prepared by hot-melt extrusion of mixtures containing high molecular weight PEO and a therapeutic compound. The present formulations cited relate to the field of non-film controlled-release drug delivery preparations, as they provide preparations useful for providing controlled drug delivery.

BACKGROUND OF THE INVENTION

Hot-melt extrusion as a method for producing polymer-based sustained-release pharmaceutical formulations, such as with derivatized cellulose, poly(methacrylate) derivative, poly(ethylene-co-vinyl acetate), poly(ethylene), poly(vinyl acetate-co-methacrylic acid), epoxy resins and caprolactones is known. These methods do not teach the use of poly(ethylene oxide). Hot-melt extrusion as a method for producing poly(ethylene glycol) based pharmaceutical formulations comprising an "erosion rate modifier" has been disclosed. These particular compositions have, been described as further containing trace amounts of high molecular weight PEO, and the hot-melt extrusion process used to prepare them requires several steps. These particular compositions are also based upon a low melting matrix drug delivery system, and are predominantly for transdermal rather than oral administration.

Alderman et al. (EP 0177893 A2) relates to a thermoformable sustained release matrix for the prolonged release of an active organic material of a thermoplastic water-soluble gel having a water-soluble hydroxypropylmethylcellulose a plasticizer and an active organic material dispersed in said gel. The plasticizer may be a low molecular weight poly(ethylene glycol).

Mooney et al. (EP 0598606 A1) relates to compositions of a thermoplastic water-soluble polymer; a water-soluble polymer derived from a carboxylic acid or a pharmaceutically acceptable salt thereof; and a plasticizer. The thermoplastic water-soluble polymer may be poly(ethylene oxide), and the compositions can be prepared as hot-melts.

These various methods require several components to achieve a desired controlled release profile. Various technical disadvantages exist for each of them that creates a significant potential for loss in pharmacological activity of the included therapeutic agent.

Hot-melt extrusion processes in the art have generally required elevated temperatures. Elevated temperatures in processing have been recognized by those in the pharmaceutical formulation arts to cause decomposition of the therapeutic agent or polymer matrix. The process of hot-melt extrusion of a therapeutic agent and a high molecular weight polymer PEO has been primarily confined to the preparation of film-like preparations.

Although various hot-melt extrusion pharmaceutical formulations and methods for making them are known, development of simple formulations for drug delivery and methods for producing them remains a problem in the pharmaceutical industry.

There continues to exist a need in the art to develop controlled-release pharmaceutical formulations, as well as improved, more efficient methods for their preparation.

SUMMARY OF THE INVENTION

In one aspect of the present invention comprises a hot-melt extrudable controlled-release pharmaceutical formulation. This formulation in some embodiments is further described as comprising an effective amount of a therapeutic compound and a high molecular weight poly(ethylene oxide) homopolymer.

It is an object of the present invention to provide a hot-melt extrudable controlled-release pharmaceutical formulation comprising high molecular weight poly(ethylene oxide) and an effective amount of a therapeutic compound.

It is another object of the present invention to provide a hot-melt extrudable controlled-release pharmaceutical formulation comprising high molecular weight poly(ethylene oxide), an effective amount of a therapeutic compound and a plasticizer. By way of example, the plasticizer may comprise poly(ethylene glycol).

It is contemplated and within the scope of the present invention that the pharmaceutical formulation may be administered to a subject by any of a variety of methods known to the artisan. In some embodiments, the formulations are designed to be particularly well suited for oral delivery.

It is also contemplated and within the scope of the present invention that the pharmaceutical formulation may comprise other components.

The methods provided on some aspects of the present invention may comprise a single step or multiple steps for preparing the pharmaceutical formulation.

It is also contemplated that the particular combinations of therapeutic compound and PEO (of given molecular weight) will result in various formulations, each possessing a particular combination of properties. Some combinations may be better suited for particular types or classes of therapeutic compounds while another combination may be better suited for other types or classes of therapeutic compounds. Methods for the selection of a particular therapeutic compound/PEO (of a given molecular weight) combination are also provided as part of the present invention.

Some embodiments of the invention comprise a plasticizer. The particular combinations of therapeutic compound/plasticizer/PEO (of given molecular weight) may be selected to provide a desired combination of physical properties. Some particular combination of these ingredients may accordingly be better suited for a particular therapeutic compound while another combination may be better suited for a different therapeutic compound. Methods for the selection of a particular therapeutic compound/plasticizer/ PEO (of a given molecular weight) combination are also disclosed as part of the present invention.

Another aspect of the invention provides a process for preparing a controlled-release pharmaceutical formulation comprising a therapeutic compound and a high molecular weight poly(ethylene oxide) homopolymer. The process in some embodiments comprises hot-melt extruding a pharmaceutical formulation. The pharmaceutical formulation comprises a therapeutic compound and a high molecular weight poly(ethylene oxide) homopolymer.

Other embodiments of the present controlled-release pharmaceutical formulations comprise a therapeutic compound and a high molecular weight poly(ethylene oxide) homopolymer, where the formulation is prepared by hot-melt extruding a mixture of its components.

In some embodiments, the pharmaceutical formulations of the invention may contain more than one therapeutic compound, as well as other non-therapeutic compound components. The pharmaceutical formulations may be formulated to provide sustained, extended, controlled, timed or other equivalent release dosage forms.

Other features, advantages and embodiments of the invention will be apparent to those skilled in the art from the following description, accompanying data and appended claims.

As used in the description of the present invention, the term "effective amount" is defined as an amount or dose sufficient to elicit a physiological response in vitro or in vivo

1A=● 6% CPM, 20% PEG (3,350), PEO (7.0 m)
1B=☐ 6% CPM, 20% PEG (3,350), PEO (1.0 m)

Figure 2:
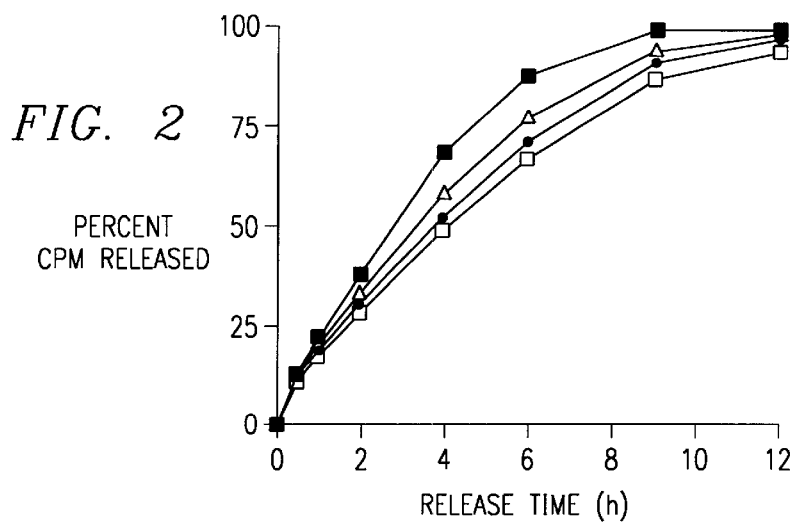

FIG. 2 Influence of polyethylene glycol (3,350) on the release of chlorpheniramine maleate from matrix tablets using USP method II at 37° C. and 100 rpm in 900 ml purified water.

2A=☐ 6% CPM, 0% PEG, (3,350) and 94% PEO (1.0 m)
2B=● 6% CPM, 6% PEG, (3,350) and 88% PEO (1.0 m)
2C=▼ 6% CPM, 20% PEG, (3,350) and 74% PEO (1.0 m)
2D=■ 6% CPM, 40% PEG, (3,350) and 54% PEO (1.0 m)

Figure 3:
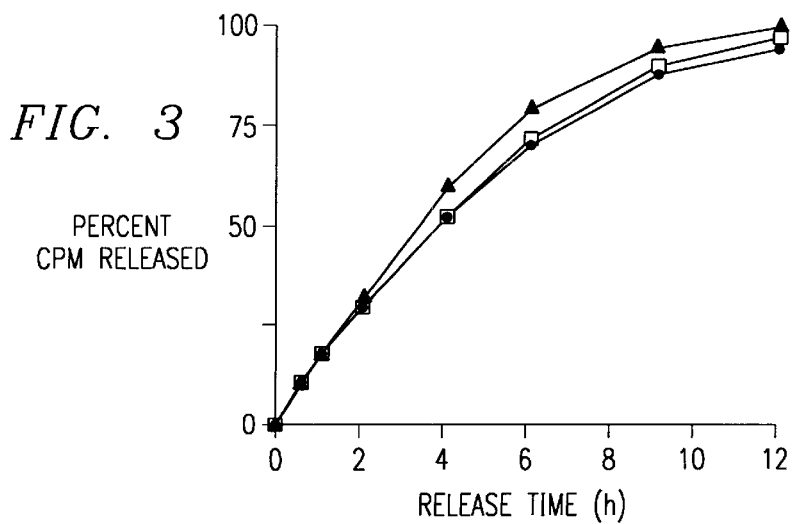

FIG. 3 Influence of drug loading on the release of chlorpheniramine maleate from matrix tablets using USP method II at 37° C. and 100 rpm in 900 ml purified water 3A=● 6% CPM, 94% PEO (1.0 m)
3B=☐ CPM, 88% PEO (1.0 m)
3C=▼ 6% CPM, 80% PEO (1.0 m)

DETAILED DESCRIPTION OF THE INVENTION

The use of hot-melt extrudable high molecular weight PEO for the preparation of pharmaceutical formulations has several advantages. The one-step process presented as part of the invention also provides therapeutic formulations with minimal thermal degradation of either the therapeutic compound or the PEO.

Poly(ethylene oxide)

As used herein, the term "poly(ethylene oxide)" includes all polymers which are comprised of repeating units of ethylene oxide. High molecular weight PEO is generally described as having an average molecular weight of from about 1,000,000 to about 10,000,000. The poly(ethylene oxides) comprising the present formulation are available commercially from sources such as Union Carbide Corporation. The amount of PEO used in the formulation will depend upon its average molecular weight, physical properties, interaction with other components of the formulation, ability to solubilize the therapeutic compound, ease of formulation extrudability, the pharmacological activity of the therapeutic compound, the indication being treated, the targeted dosing regimen, the projected method of administration, the integrity or stability of the final formulation, desired release profile or other such reasons. Generally, PEO content will not exceed about 99% wt. of the formulation.

The average molecular weight of the PEO employed will generally affect the processing conditions selected. A very high average molecular weight PEO, such as greater than about 5,000,000, will generally require higher processing temperature, torque and/or pressure than a PEO having an average molecular weight less than or equal to about 5,000,000. Antioxidants and/or plasticizers may be advantageously employed when preparing the formulation of the invention. Thus, although not required to obtain a hot-melt extrudable formulation, addition of one or more plasticizers and/or antioxidants to the formulation will generally facilitate the preparation process.

Figure 1:
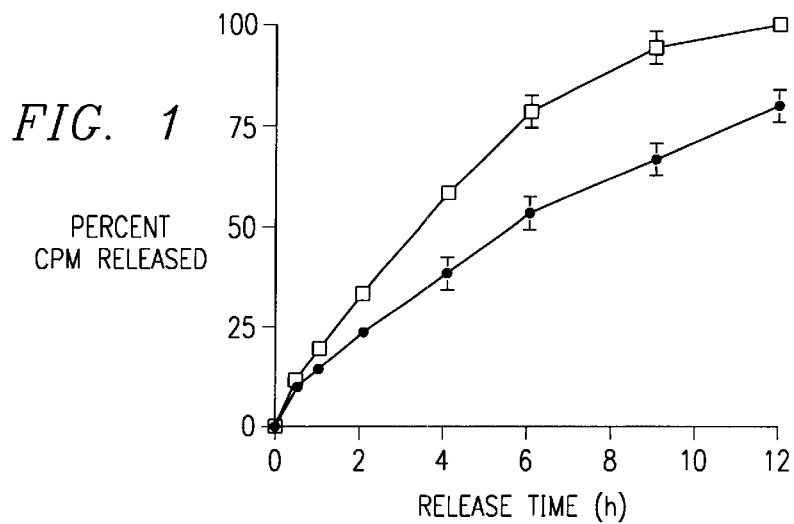
FIG. 1 Influence of molecular weight of polyethylene oxide on the release of chlorpheniramine maleate from matrix tablets using USP method II at 37° C. and 100 rpm in 900 ml purified water.

As shown in FIG. 1, PEO average molecular weight also affects the release profile of the formulation. Generally, increasing average molecular weight decreases the release rate of the therapeutic compound.

Plasticizers

As used herein, the term "plasticizer" includes all compounds capable of plasticizing high molecular weight PEO. The plasticizer should be able to lower the glass transition temperature or softening point of the PEO in order to allow for lower processing temperature, extruder torque and pressure during the hot-melt extrusion process. Plasticizers, such as PEG and low molecular weight PEO, generally broaden the average molecular weight of the PEO thereby lowering its glass transition temperature or softening point. Plasticizers also generally reduce the viscosity of a polymer melt thereby allowing for lower processing temperature and extruder torque during hot-melt extrusion. It is possible the plasticizer will impart some particularly advantageous physical properties to the pharmaceutical formulation of PEO.

As used herein, the term "low molecular weight PEO" is intended to mean poly(ethylene oxide) homopolymer having an average molecular weight less than about 500,000.

Plasticizers are not required in order to practice the invention. Their addition to the formulation is contemplated as being within the scope of the invention. Plasticizers are advantageously included when very high molecular weight PEO, such as greater than about 5,000,000, is employed.

As shown in FIG. 2, it is possible that including a plasticizer in the present formulation will alter its release profile. Generally, increasing the amount of plasticizer present will increase the release rate of the therapeutic compound.

It is contemplated and within the scope of the invention, that a combination of plasticizers may be used in the present formulation. One advantageous combination is that comprised of poly(ethylene glycol) and low molecular weight poly(ethylene oxide).

The plasticizer employed herein may be a solvent for the PEO at the temperature where the formulation is prepared. Such plasticizer, when mixed with the PEO above a characteristic temperature at which the PEO becomes soluble therein, may dissolve the PEO. Upon cooling, the mixture forms a matrix having especially useful properties for use in a sustained release dosage form.

Plasticizers useful in the invention include, by way of example and without limitation, low molecular weight polymners, oligomers, copolymers, oils, small organic molecules, low molecular weight polyols having aliphatic hydroxyls, ester-type plasticizers, glycol ethers, poly (propylene glycol), multi-block polymers, single block polymers, low molecular weight poly(ethylene oxide) (average molecular weight less than about 500,000) and poly(ethylene glycol).

Such plasticizers may be ethylene glycol, propylene glycol, 1.2-butylene glycol, 2,3-butylene glycol, styrene glycol, diethylene glycol, triethylene glycol, tetraethylene glycol and other poly(ethylene glycol) compounds, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, triethyl citrate, acetyl triethyl citrate, tributyl citrate and allyl glycolate. All such plasticizers are commercially available from sources such as Aldrich or Sigma Chemical Co.

The PEG based plasticizers are available commercially or may be made by a variety of methods, such as disclosed in *Poly (ethylene glycol) Chemistry: Biotechnical and Biomedical Applications* (J. M. Harris, Ed.; Plenum Press, NY) the teachings of which are hereby incorporated by reference.

The amount of plasticizer used in the formulation will depend upon its composition, physical properties, effect upon the PEO, interaction with other components of the formulation, ability to solubilize the therapeutic compound or other factors to be considered in the preparation of pharmaceutical formulations. The amount of plasticizer present in the formulation affects its properties. By way of example, when the plasticizer is PEG, its content will generally not exceed about 40% wt. of the formulation.

When present, the relative amount of plasticizer used may be expressed by the ratio high molecular weight PEO % wt.: plasticizer % wt., and will generally fall in the range of about 100:0 to about 60:40. The amount of plasticizer will generally not exceed the amount of PEO.

Therapeutic Preparations

As used herein, the term "therapeutic compound" is taken to mean an organic chemical substance having desired beneficial and therapeutic effects in mammals. Such compounds are generally classified as pharmaceuticals or biologicals. As long as the therapeutic compound can diffuse from the formulation when exposed to a biological fluid, its structure is not especially critical.

The therapeutic compounds contemplated within the scope of the invention include hydrophobic, hydrophilic and amphiphilic compounds. They may be in their free acid, free base, or pharmaceutically acceptable salt forms. They may be derivatives or prodrugs of a given pharmaceutical.

It will be appreciated that certain therapeutic compounds used in the present invention may contain an asymmetrically substituted carbon atom, and may be isolated in optically active or racemic forms. It is well known in the art how to prepare optically active forms, such as by resolution of racemic forms or by synthesis, from optically active starting materials. Also, it is realized that cis and trans geometric isomers of the therapeutic compounds are described and may be isolated as a mixture of isomers or as separated isomeric forms. All chiral, diastereomeric, racemic forms and all geometric isomeric forms of a structure are intended, unless the specific stereochemistry or isomer form is specifically indicated.

It is not necessary for the therapeutic compound to be soluble in any given formulation component. The therapeutic compound may be either dissolved, partially dissolved or suspended in the polymer matrix of the formulation. It is necessary for the therapeuticcompound to be stable during the hot-melt extrusion process conditions used. By stable, it is meant that a significant portion of the therapeutic compound will not be significantly degraded or decomposed throughout the hot-melt extrusion process.

The therapeutic compounds which may be hot-melt extruded in the formulation of the invention may be used for treating indications such as, by way of example and without limitation, inflammation, gout, hypercholesterolemia, microbial infection, AIDS, tuberculosis, fungal infection, amoebic infection, parasitic infection, cancer, tumor, organ rejection, diabetes, heart failure, arthritis, asthma, pain, congestion, urinary tract infections, vaginal infection, seizure related disorder, depression, psychosis, convulsion, diabetes, blood coagulation, hypertension and birth control.

The following therapeutic compounds can be administered by the pharmaceutical formulation of the present invention:

(1) analgesics such as aspirin, acetaminophen, deflunisal and the like;

(2) anesthetics such as lidocaine, procaine, benzocaine, xylocaine and the like;

(3) antiarthritics and anti-inflammatory agents such as phenylbutazone, indomethacin, sulindac, dexamethasone, ibuprofen, allopurinol, oxyphenbutazone probenecid, cortisone, hydrocortisone, betamethasone, dexamethasone, fluocortolone, prednisolone, triamncinolone, indomethacin, sulindac and its salts and corresponding sulfide and the like;

(4) antiasthma drugs such as theophylline, ephedrine, beclomethasone dipropionate, epinephrine and the like;

(5) urinary tract disinfectives such as sulfarmethoxazole, trimethoprim, nitrofurantoin, norfloxicin and the like;

(6) anticoagulants such as heparin, bishydroxy coumarin, warfarin and the like;

(7) anticonvulsants such as diphenylhydantoin, diazepam and the like;

(8) antidepressants such as amitriptyline, chlordiazepoxide, perphenazine, protriptyline, imipramine, doxepin and the like;

(9) agents useful in the treatment of diabetics and regulation of blood sugar, such as insulin, tolbutamide tolazamide, somatotropin, acetohexamide, chlorpropamide and the like;

(10) antineoplastics such as adriamycin, fluouracil, methotrexate, asparaginase and the like;

(11) antipsychotics such as prochlorperazine, lithium carbonate, lithium citrate, thioridazine, molindone, fluphenazine, trifluoperazine, perphenazine, amitriptyline, triflupromazine and the like;

(12) antihypertensives such as spironolactone, methyldopa, hydralazine, clonidine, chlorothiazide, deserpidine, timolol, propranolol, metaprotol, prazosin hydrochloride, reserpine and the like;

(13) muscle relaxants such as mephalan, danbrolene, cyclobenzaprine, methocarbarnol, diazepam, succinoyl chloride and the like;

(14) antiprotozoals such as chloramphenicol, chloroquine, trimethoprim and sulfamethoxazole;

(15) spermicidals such as nonoxynol;

(16) antibacterial substances such as beta-lactam antibiotics, tetracyclines, chloramphenicol, neomycin, cefoxitin, thienamycin, gramicidin, bacitracin, sulfonamides, aminoglycoside antibiotics, tobramycin, nitrofurazone, nalidixic acid and analogs and the antimicrobial combination of fludalanine/pentizidone;

(17) antihistamines and decongestants such as perilamine, chlorpheniramine, tetrahydrozoline and antazoline;

(18) antiparasitic compounds such as ivermectin; and

(19) antiviral compounds such as acyclovir and interferon.

For treatment of vaginal and urethral conditions requiring antiftungal, amoebicidal, trichomonacidal agents or antiprotozoals, the following agents can be used: polyoxyethylene nonylphenol, alkylaryl sulfonate, oxyquinoline sulfate, miconazole nitrate, sulfanilamide, candicidin, sulfisoxazole, nysatitin, clotrimazole, metronidazole and the like.

Loading of the therapeutic compounds into the final formulation may be accomplished following the techniques below. Generally, the therapeutic compound is loaded by premixing it with PEO and any other formulation components and hot-melt extruding the mixture. The mixture may be either a solution, slurry, suspension or solid. When solids are present in the mixture, they may be, by way of example and without limitation, either powdered, crystalline, amorphous, pelletized, beaded, spheronized, granular or the like.

It should be understood that the amount of therapeutic compound loaded into the formulation may be varied according to, for example, the high molecular weight PEO-:therapeutic compound or the high molecular weight PEO:plasticizer:therapeutic compound ratios used in the pre-extruded mixture. Although a given loading method may be optimal for a particular high molecular weight PEO-:therapeutic compound combination, all of the described methods will generally result in compound loading to some degree.

The therapeutic amount of compound loaded into the formulation will vary according to the pharmacological activity of the compound, the indication being treated, the targeted dosing regimen, the projected method of administration, the integrity or stability of the final formulation or other such reasons.

As shown in FIG. 3, the amount of therapeutic compound loaded into the formulation will generally have only a marginal effect upon the release profile of therapeutic compound. In this particular embodiment, a 300 mg tablet contained high molecular weight PEO (about 60, or about 80- to about 90, or about 94% wt., MW 1,000,000) and chlorpheniramine maleate (about 5, or about 6- to about 200% wt.) . The formulation was prepared following the procedure described in Example 3, and the release profile was determined following the procedure described in Example 1. In some embodiments, the compound loading into the formulation of the invention will not exceed about 20% wt. of the final formulation.

Hot-Melt Extrusion Process

As used herein, the term "hot-melt extrudable" refers to a compound or formulation that may be hot-melt extruded. A hot-melt extrudable polymer is one that is sufficiently rigid at standard ambient temperature and pressure but is capable of deformation or forming a semi-liquid state under elevated heat or pressure. Although the formulation of the invention need not contain a plasticizer to render it hot-melt extrudable, plasticizers of the type described herein may be included and still remain within the scope of the invention.

Although the process referred to above has been called a hot-melt extrusion, other equivalents processes such as injection molding, hot dipping, melt casting and compression molding may be used. By using any of these methods, the formulation may be shaped as needed according to the desired mode of administration, e.g. tablets, pills, lozenges, suppositories and the like.

The hot-melt extrusion process employed in some embodiments of the invention is conducted at an elevated temperature, i.e. the heating zone(s) 20 of the extruder is above room temperature (about 20° C.). It is important to select an operating temperature range that will minimize the degradation or decomposition of the therapeutic compound during processing. The operating temperature range is generally in the range of from about 60° C. to about 160° C. as determined by the setting for the extruder heating zone(s).

In some embodiments of the invention, the hot-melt extrusion may be conducted employing a slurry, solid, suspension, liquid, powdered or other such feed comprising PEO and a therapeutic compound. Dry feed is advantageously employed in the process of the present invention.

The hot-melt extrusion process is generally described as follows. An effective amount of a powdered therapeutic compound is mixed with a high molecular weight PEO, and in some embodiments, with a plasticizer such as PEG. Other components may be added in the various embodiments of the invention. In some embodiments, the therapeutic compound: PEO ratio is generally about 0.01: about 99.99 to about 20: about 80% wt., depending on the desired release profile, the pharmacological activity and toxicity of the therapeutic compound and other such considerations. The mixture is then placed in the extruder hopper and passed through the heated area of the extruder at a temperature which will melt or soften the PEO and/or plasticizer, if present, to form a matrix throughout which the therapeutic compound is dispersed. The molten or softened mixture then exits via a die, or other such element, at which time, the mixture (now called the extrudate) begins to harden. Since the extrudate is still warm or hot upon exiting the die, it may be easily shaped, molded, chopped, ground, molded, spheonized into beads, cut into strands, tableted or otherwise processed to the desired physical form.

The extruder used to practice the invention may be any such commercially available model equipped to handle dry feed and having a solid conveying zone, one or multiple heating zones, and an extrusion die. A two stage single screw extruder, such as that manufactured by C.W. Brabender Instruments Incorporated (NJ) is one such apparatus. It is particularly advantageous for the extruder to possess multiple separate temperature controllable heating zones.

Many conditions may be varied during the extrusion process to arrive at a particularly advantageous formulation. Such conditions include, by way of example, formulation composition, feed rate, operating temperature, extruder screw RPM, residence time, die configuration, heating zone length and extruder torque and/or pressure. Methods for the optimization of such conditions are known to the skilled artisan.

When very high molecular weight PEO, such as greater than about 5,000,000, is employed, the hot-melt extrusion may require higher processing temperature, pressure and/or torque than when PEO having a molecular weight less than or equal to about 5,000,000 is employed. By including a plasticizer, and, optionally, an antioxidant, in a formulation comprising very high molecular weight PEO, processing temperature, pressure and/or torque may be reduced.

Pharmaceutical Compositions and Their Administration

The pharmaceutical formulation of the present invention may be administered by a variety of methods. Such methods include, by way of example and without limitation: oral, nasal, buccal, rectal, ophthalmic, otic, urethral, vaginal, or sublingual dosage administration. Such methods of administration and others contemplated within the scope of the present invention are known to the skilled artisan.

In vivo stability of the present formulation may vary according to the physiological environment to which it is exposed and the specific therapeutic compound, PEO and plasticizer used. Therefore, the necessity for or frequency of readministration may be different for various formulations.

The pharmaceutical formulation of the present invention may be provided in a variety of ways. Additional components that would not significantly prohibit the hot-melt extrusion process may be added to the formulation prior to hot-melt extrusion. The additional components would still allow for the high molecular weight PEO: therapeutic compound mixture to be formulated using a hot-melt extrusion process.

For nasal administration, the pharmaceutical formulation may be a paste, cream or ointment containing the appropriate solvents (such as water, aqueous, nonaqueous, polar, nonpolar, hydropic, hydrophilic and/or combinations thereof) and optionally other compounds (stabilizers, perfumes, antimicrobial agents, antioxidants, pH modifiers, surfactants and/or bioavailability modifiers). It is contemplated that bioavailability enhancers such as alcohols or other compounds that enhance the penetration of the therapeutic compound from the pharmaceutical formulation into the nasal mucosa may be needed to prepare suitable formulations for nasal administration.

For oral, buccal, and sublingual administration, the pharmaceutical formulation may be in the form of a gel cap, caplet, tablet, capsule, suspension or powder. For rectal administration, the pharmaceutical formulation may be in the form of a suppository, ointment, enema, tablet or cream for release of compound into the intestines, sigmoid flexure and/or rectum.

In solid unit dosage forms, the compounds can be combined with conventional carriers, for example: binders, such as acacia, corn starch or gelatin; disintegrating agents, such as, corn starch, guar gum, potato starch or alginic acid; lubricants, such as stearic acid or magnesium stearate; and inert fillers, such as lactose, sucrose or corn starch.

In some embodiments of the invention, the term "unit dosage form" is used herein to mean a single or multiple dose form containing a quantity of the therapeutic compound containing formulation, said quantity being such that one or more predetermined units may be provided as a single therapeutic administration. In the case of multiple dose forms, such as suspensions or scored tablets, said predetermined unit will be one fraction of a prescribed full dosage regimen, i.e. a 5 ml (teaspoon) quantity of a prescribed 100 mL suspension.

The pharmaceutical formulations may also be administered as solutions or liquid suspensions comprising high molecular weight PEO, a therapeutic compound and a sterile liquid, such as an oil, water, an alcohol, or mixtures thereof, with or without the addition of pharmaceutically suitable surfactants, suspending agent, or emulsifying agent for oral or parenteral administration.

For suspension preparations, the pharmaceutical formulation may include oils, for example, fixed oils, such as peanut oil, sesame oil, cottonseed oil, corn oil and olive oil; fatty acids, such as oleic acid, stearic acid and isotearic acid; and fatty acid esters, such as ethyl oleate, isopropyl myristate, fatty acid glycerides and acetylated fatty acid glycerides. They may also be mixed with alcohols, such as ethanol, isopropanol, hexadecyl alcohol, glycerol and propylene glycol; with glycerol ketals, such as 2,2-dimethyl-1, 3-dioxolane-4-methanol; with ethers, such as poly(ethylene glycol) 450, with petroleum hydrocarbons, such as mineral oil and petrolatum; with water, or with mixtures thereof; with or without the addition of a pharmaceutically suitable surfactant, suspending agent or emulsifying agent.

Oils can also be employed in the preparation of formulations of the soft gelatin type and suppositories. Water, saline, aqueous dextrose and related sugar solutions, and glycerols may be employed in the preparation of suspension formulations which may suitably contain suspending agents, such as pectin, carbomers, methyl cellulose, hydroxypropyl cellulose or carboxymethyl cellulose, as well as buffers and preservatives. Soaps and synthetic detergents may be employed as surfactants and as vehicles for detergent compositions. Suitable soaps include fatty acid alkali metal, ammonium, and triethanolamine salts. Suitable detergents include cationic detergents, for example, dimethyl dialkyl ammonium halides, alkyl pyridinium halides, and alkylamine acetates; anionic detergents, for example, alkyl, aryl and olefin sulfonates, alkyl, olefin, ether and monoglyceride sulfates, and sulfosuccinates; nonionic detergents, for example, fatty amine oxides, fatty acid alkanolamides, and poly(oxyethylene)-block-poly(oxypropylene) copolymers; and amphoteric detergents, for example, alkyl β-aminopropionates and 2-alkylimidazoline quaternary ammonium salts; and mixtures thereof.

It is contemplated that either one or a combination of long-acting, sustained release, controlled release or slow release dosage forms may be used in the present invention. The course and duration of administration of and the dosage requirements for the formulation of the present invention will vary according to the subject being treated, the compound being administered, the formulation used, the method of administration used, the severity and type of indication being treated, the coadministration of other drugs and other factors.

The therapeutic compounds contained within the formulation may be formulated as their pharmaceutically acceptable salts. As used herein, "pharmaceutically acceptable salts" refers to derivatives of the disclosed compounds wherein the parent therapeutic compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfonic, sulfamic, phosphoric, nitric and the like; and the salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, flunaric, toluenesulfonic, methanesulfonic, ethane disulfonic, oxalic, isethionic, and the like.

The pharmaceutically acceptable salts of the present invention can be synthesized from a parent therapeutic compound which contains a basic or acidic moiety by conventional chemical methods. Generally, such salts can be prepared by reacting the free acid or base forms of these compounds with a predetermined amount of the appropriate base or acid in water or in an organic solvent, or in a mixture of the two. Generally, nonaqueous media are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Some embodiments of the invention comprise a hot-melt extrudable controlled-release pharmaceutical formulation comprising an effective amount of a therapeutic compound, high molecular weight poly(ethylene oxide) and a plasticizer. By way of example, the poly(ethylene oxide) may be further defined as having a molecular weight average in the range of from about 1,000,000 to about 10,000,000.

In other embodiments, the invention provides a hot-melt extrudable controlled-release pharmaceutical formulation comprising an effective amount of a therapeutic compound, high molecular weight poly(ethylene oxide) and a plasticizer. The poly(ethylene oxide) may be further defined as having a molecular weight average in the range of from about 1,000,000 to about 10,000,000. In some embodiments, the amount of the poly(ethylene oxide) and the therapeutic compound may be defined as a ratio. By way of example, this ratio may be defined as in the range of from about 99.99:01 to about 80:20% wt. Some of these compositions may include a plasticizer selected from the group consisting of: low molecular weight polymers, oligomers, or copolymers, oils, small organic molecules, low molecular weight polyols having aliphatic hydroxyls, ester-type plasticizers, glycol ethers, poly(propylene glycol), multi-block polymers, single block polymers, low molecular weight poly(ethylene oxide) (molecular weight less than about 500,000) and poly(ethylene glycol).

In other embodiments, the invention provides a hot-melt extrudable controlled-release pharmaceutical formulation comprising an effective amount of a therapeutic compound, high molecular weight poly(ethylene oxide) and a plasticizer. The poly(ethylene oxide) may be further defined as having a molecular weight average in the range of from about 1,000,000 to about 7,000,000. The poly(ethylene oxide):therapeutic compound ratio being in the range of from about 99.99:0.01 to about 80:20% wt. The plasticizer in some of these formulations may comprise poly(ethylene glycol). The poly(ethylene oxide) poly(ethylene glycol) ratio may be defined as being in the range of from about 99.99:0.01 to about 60:40% wt.

In other embodiments, the present invention provides a hot-melt extrudable controlled-release pharmaceutical formulation comprising an effective amount of a therapeutic compound and high molecular weight poly(ethylene oxide). The poly(ethylene oxide) of these formulations may be defined as having a molecular weight average in the range of from about 1,000,000 to about 10,000,000. These formulations may be prepared by hot-melt extruding the therapeutic compound and the high molecular weight poly(ethylene oxide).

Unless otherwise indicated, all chemicals were purchased from Aldrich Chemicals (Milwaukee, Wis.).

The following abbreviations are used in the description of the invention:

| | |
|---|---|
| EO | ethylene oxide; |
| GPC | gel permeation chromatography; |
| MW | molecular weight; |
| PEO | poly (ethylene oxide); and |
| PEG | poly (ethylene glycol). |

Following long-standing patent law convention, the terms "all and "an" mean "one or more" when used in this application, including the claims.

The following examples provide a detailed description of particular embodiments of the invention. It is recognized that departures from the disclosed embodiment may be made within the scope of the invention and that obvious modifications will occur to a person skilled in the art. The full scope of the invention is set out in the claims that follow and their equivalents. Accordingly, the claims and specification should not be construed to unduly narrow the full scope of protection to which the invention is entitled.

EXAMPLE 1

Method for the Determination of Therapeutic Compound Release Rate

The therapeutic compound release rate was generally determined as follows and as described in USP 23 NF18 (pages 1791–1792), method 711, apparatus II, which reference is specifically incorporated herein by reference for this purpose. The formulation was placed in water (100 mL at 37° C.) in a flask while stirring to form a dilute suspension. Aliquots of the suspension solution were drawn from the flask at intervals and filtered to remove suspended solids. The supernatant was then analyzed by HPLC and the concentration of therapeutic compound in solution quantified. By repeating this procedure, the release profile for various formulations was determined.

EXAMPLE 2

Preparation of A Therapeutic Compound/Poly (ethylene oxide) Formulation

An amount of losoxanthrone solid sufficient to provide an effective amount of the formulation may be mixed with a known amount of PEO polymer. The weight ratio of losoxanthrone:polymer may be about 5:95% wt. The solid mixture may then be placed in an extruder hopper. The extruder to be used should include a solids-conveying mechanism that extends from the hopper through a heating zone to the extrusion die. The solid mixture is passed through the heated extruder at a temperature range of about 1000 to about 140° C., as determined by the temperature setting of the extruder heating zone so that melting or softening of the PEO occurs. Upon exiting the die, the extrudate (PEO/losoxanthrone) may be chopped to the desired length. The extrudate may then be ground to a powder or molded to a caplet prior to final formulation.

EXAMPLE 3

Preparation of A Therapeutic Compound/Poly (ethylene oxide) Formulation

Chlorpheniramine maleate (9.6 g) may be mixed with poly(ethylene glycol) (32.0 g, molecular weight average 3.350) in a twin-shell blender for five minutes. Poly (ethylene oxide) (118.4 g, molecular weight average 1,000, 000) may then be added and the entire mixture stirred for about 10 minutes. The solid mixture may then be placed in an extruder hopper. The extruder to be used may have a single screw solids conveying mechanism that extends from the hopper through multiple heating zones to the extrusion die, the die having a 1 cm diameter. The solid mixture may then be passed through the heated extruder at a temperature range of about 75° C. to about 130° C., as determined by the temperature setting of the extruder heating zones so that melting or softening of the PEO occurred. An extruder torque of 34 (Nm) and screw speed of 25 r.p.m. may then be used. Upon exiting the die, the extrudate may be chopped to form tablets about 0.6 cm thick. The release rate profile of cpm may be determined for the formulation using the method of Example 1.

EXAMPLE 4

Preparation of Various Therapeutic Compound/Poly (ethylene oxide) Formulations Various other formulations may be prepared using the method of Example 3. The composition and processing conditions used for these formulations is summarized in the table below. The chlorpheniramine maleate concentration will be kept constant at about 6% wt. for the following examples. The amounts of PEO and PEG may be varied. The molecular weight average of the PEG may be kept constant at 3,350. The molecular weight average of the PEO may be varied.

| Composition | | Heating Zone 1 | Heating Zone 2 | Die | | Screw |
|---|---|---|---|---|---|---|
| PEG (% wt) | PEO (% wt, MW) | Temp. (deg C.) | Temp. (deg C.) | Temp (deg C.) | Torque (Nm) | Speed (rpm) |
| 0 | 94, 1,000,000 | 110 | 115 | 130 | 34 | 25 |
| 6 | 88, 1,000,000 | 110 | 115 | 130 | 28 | 25 |
| 20 | 74, 1,000,000 | 70 | 75 | 85 | 23 | 25 |
| 40 | 54, 1,000,000 | 70 | 70 | 85 | 10 | 25 |
| 0 | 94, 7,000,000 | 135 | 140 | 145 | 35 | 25 |
| 20 | 74, 7,000,000 | 90 | 90 | 100 | 21 | 25 |

REFERENCES

The following references, to the extent they provide exemplary procedural or other details supplementary to those set forth herein, are specifically hereby incorporated by reference.

1) G. Bechmann, Ueber die verzogerte Wirkstoff-Freigabe aus peroralen, festen Arzneiformen (Ph.D. Thesis, University of Frankfort, 1964);
2) El-Egakey et al., *Pharm. Acta. Helv.* (1971), 46, 31–52;
3) Hüttenrauch et al., *Pharmazie* (1975), 229–233;
4) Rippie et al., *J. Pharm. Sci.* (1969), 428–431;
5) Shivanand et al., *Pharm. Res.* (1991),S-192;
6) Prapaitrakul et al., *Pharm. Res.* (1989), 6, S-98;
7) Mank et al., *Pharmazie* (1989), 44, 773–776;
8) Mank et al., *Pharmazie* (1990), 45, 592–593;
9) Follonier et al., *Drug Develop. and Indust. Pharm.*, (1994), 20(8), 1323–1339;
10) W. C. Snipes, U.S. Pat. No. 5,004,601;
11) U.S. Pat. No. 4,806,337;
12) U.S. Pat. No. 4,774,074;
13) U.S. Pat. No. 4,774,976;
14) U.S. Pat. No. 4,629,621;
15) Poly(ethylene glycol) Chemistry: Biotechnical and Biomedical Applications (J. M. Harris Ed., Plenum Press, NY);
16) Remington's Pharmaceutical Sciences, 17th ed. (Mack Publishing Co., Easton, Pa., 18042, 1985);
17) Goodman & Gilman's: The Pharmacological Basis of Therapeutics, 7th ed. (A. Goodman Gilman, L. S. Goodman, T. W. Rall & F. Murad Ed.s, MacMillan Publishing Co., NY, 1985).

What is claimed is:

1. A non-film controlled release pharmaceutical formulation comprising an effective amount of a therapeutic compound and a high molecular weight poly(ethylene oxide), wherein the poly(ethylene oxide) has a molecular weight of about 1,000,000 to about 10,000,000 Daltons, and wherein the poly(ethylene oxide) and the therapeutic compound comprise a ratio of poly(ethylene oxide) to therapeutic compound of from about 99.99:.01 weight percent to about 50:50 weight percent.

2. The non-film controlled release pharmaceutical formulation of claim 1 further comprising a plasticizer.

3. The non-film controlled release formulation of claim 2 wherein the plasticizer is selected from the group consisting of: an oligomer, a copolymer, an oil, a organic molecule, a polyol having aliphatic hydroxyls, an ester-type plasticizer, a glycol ether, poly(propylene glycol), a multi-block polymer, a single block polymer, and a poly(ethylene oxide) having a molecular weight less than about 500,000 Daltons.

4. The non-film controlled release pharmaceutical preparation of claim 3, wherein the polyethythene oxide is further defined as polyethylene oxide having a molecular weight less than about 500,000 Daltons.

5. The non-film controlled release pharmaceutical formulation of claim 4, further comprising poly(ethylene glycol).

6. The non-film controlled release pharmaceutical formulation of claim 1 wherein said formulation is prepared by a process of hot-melt extrusion.

\* \* \* \* \*